United States Patent
Amundson et al.

[11] Patent Number: 5,899,934
[45] Date of Patent: May 4, 1999

[54] DUAL STENT

[75] Inventors: Rodney R. Amundson, Lindstrom; Eric P. Berg, Plymouth, both of Minn.

[73] Assignee: Medtronic, Inc, Minneapolis, Minn.

[21] Appl. No.: 08/791,209

[22] Filed: Jan. 31, 1997

[51] Int. Cl.$^6$ .................................................. A61F 2/06
[52] U.S. Cl. ................................ 623/1; 623/12; 606/194; 606/198
[58] Field of Search .................. 623/1, 12; 606/194, 606/195, 191, 198

[56] References Cited

U.S. PATENT DOCUMENTS

| | | | |
|---|---|---|---|
| 4,856,516 | 8/1989 | Hillstead | 128/343 |
| 4,878,906 | 11/1989 | Lindemann et al. | 623/1 |
| 4,886,062 | 12/1989 | Wiktor | 128/343 |
| 4,994,071 | 2/1991 | MacGregor | 606/194 |
| 5,133,732 | 7/1992 | Wiktor | 606/195 |
| 5,135,536 | 8/1992 | Hillstead | 606/195 |
| 5,217,483 | 6/1993 | Tower | 606/198 |
| 5,389,106 | 2/1995 | Tower | 606/198 X |
| 5,843,168 | 12/1998 | Dang | 623/1 |

FOREIGN PATENT DOCUMENTS

| | | | |
|---|---|---|---|
| WO 92/09246 | 6/1992 | WIPO | 623/1 |

*Primary Examiner*—David H. Willse
*Assistant Examiner*—Suzette J. Jackson
*Attorney, Agent, or Firm*—Dianne Plunkett Latham; Harold R. Patton

[57] ABSTRACT

A medical device for use in supporting a luminal surface of a human or animal body comprising a catheter, a stent mounted on the distal end of the catheter, the stent comprising a hollow cylindrical first wire segment and a hollow cylindrical second wire segment, and a means on the catheter for releasing the stent in the expanded diameter from the catheter. The first wire segment forms a plurality of spaced-apart first wire segment elements each extending 360 degrees around the hollow cylinder, each of the first wire segment elements having a plurality of extendible portions which permit the first wire segment elements to be expanded from the unexpanded diameter to a second, expanded diameter, the first wire segment proximal end having a straight tail extending proximally and longitudinally therefrom. The second wire segment forming a plurality of spaced-apart second wire segment elements each extending 360 degrees around the hollow cylinder, each of the second wire segment elements having a plurality of extendible portions which permit the second wire segment elements to be expanded from the unexpanded diameter to a second, expanded diameter, the second wire segment distal end having a straight tail extending distally and longitudinally therefrom.

11 Claims, 2 Drawing Sheets

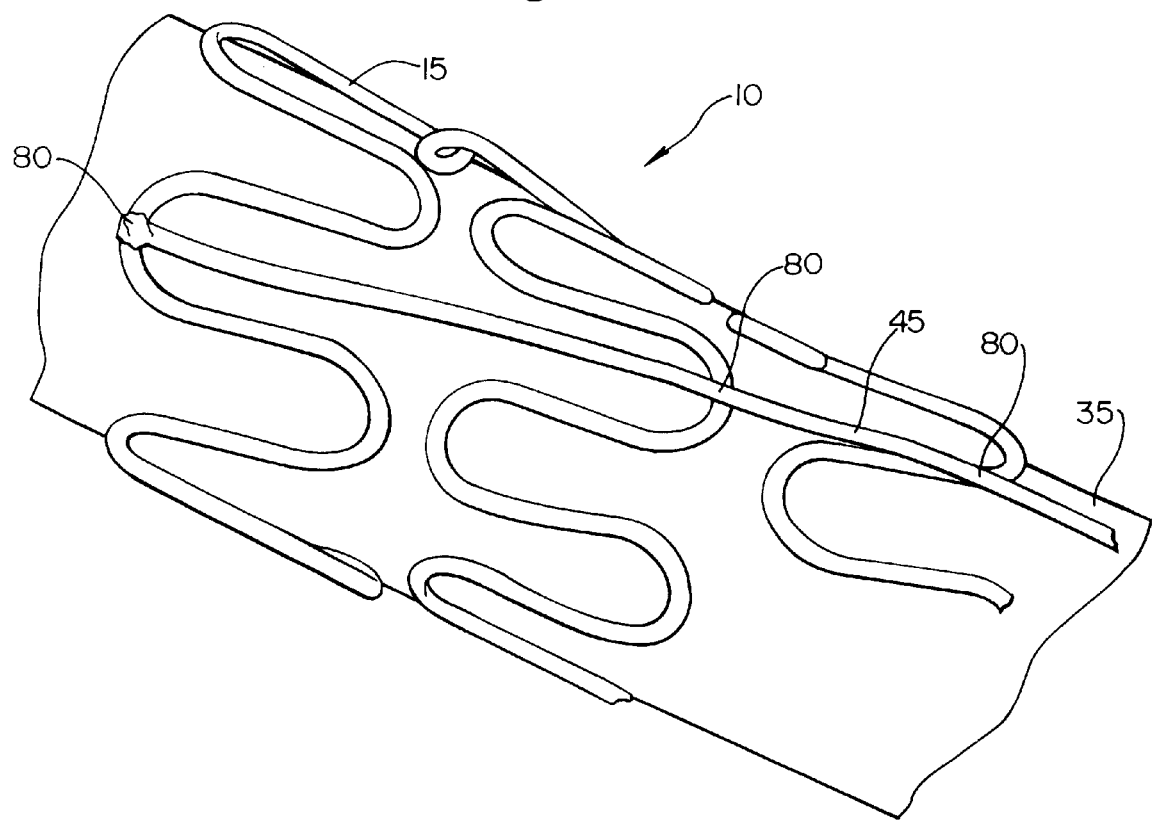

DUAL STENT

FIELD OF THE INVENTION

The present invention relates to intravascular stent implants for maintaining vascular patency in humans and animals and more particularly to a stent in the form of two joined half stents with counterpart ribs.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent 10 ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the interior of the body lumen thereby forming a supporting relationship with the vessel walls.

Various shapes of stents are known in the art. U.S. Pat. No. 4,886,062 to Wiktor for "Intravascular Radially Expandable Stent and Method of Implant" discloses a two-dimensional zig-zag form, typically a sinusoidal form.

U.S. Pat. No. 4,856,516 to Hillstead for "Endovascular Stent Apparatus and Method" discloses a wire first bent into a series of tight bends. The wire is then further bent into a sequence of loops that are connected by half hitch junctions and interconnections which are either aligned or spiral around a circumference of the stent.

U.S. Pat. No. 4,878,906 to Lindemann et al. for "Endoprosthesis for Repairing a Damaged Vessel" discloses a flexible, plastic, thin-walled sleeve molded with various types of circumferential and axial ribs and reinforcements to be used as an endovascular prosthesis.

U.S. Pat. No. 4,994,071 to MacGregor for "Bifircating Stent Apparatus and Method" discloses a wire forming a backbone extending axially along the length of the lattice that extends away from the lattice and is used to construct the interconnecting loops.

U.S. Pat. No. 5,133,732 to Wiktor for "Intravascular Stent" discloses a stent body coiled from a generally continuous wire with a deformable zig-zag structure with a means for preventing the stent body from stretching along its longitudinal axis.

The above art discloses various axial ribs. The disadvantage of such single longitudinal reinforcements is that of reduced flexibility. What is needed is a stent design which controls the length of the stent as it expands on a balloon yet maintains flexibility without resulting in longitudinal compression at the center of the stent when expanded.

SUMMARY OF THE INVENTION

It is an object of the invention to provide a wire wound stent having good wire coverage and hoop strength which controls the length of the stent as is expands on a balloon yet maintains flexibility without resulting in longitudinal compression at the center of the stent when expanded.

The present invention is accomplished by providing a medical device for use in supporting a luminal surface of a human or animal body comprising a catheter, a stent mounted on the distal end of the catheter, the stent comprising a hollow cylindrical first wire segment and a hollow cylindrical second wire segment, and a means on the catheter for releasing the stent in the expanded diameter from the catheter. The first wire segment forms a plurality of spaced-apart first wire segment elements each extending 360 degrees around the hollow cylinder, each of the first wire segment elements having a plurality of extendible portions which permit the first wire segment elements to be expanded from the unexpanded diameter to a second, expanded diameter, the first wire segment proximal end having a straight tail extending proximally and longitudinally therefrom. The second wire segment forming a plurality of spaced-apart second wire segment elements each extending 360 degrees around the hollow cylinder, each of the second wire segment elements having a plurality of extendible portions which permit the second wire segment elements to be expanded from the unexpanded diameter to a second, expanded diameter, the second wire segment distal end having a straight tail extending distally and longitudinally therefrom. The proximal end of the first wire segment is abutted to the distal end of the second wire segment such that the tail of the first wire segment longitudinally extends along the length of the second wire segment and the tail of the second wire segment longitudinally extends along the length of the first wire segment with one or more elements of the first wire segment being attached to the tail of the second wire segment, each such attachment forming a second wire segment crossing. One or more elements of the second wire segment is attached to the tail of the first wire segment, each such attachment forming a first wire segment crossing.

BRIEF DESCRIPTION OF THE DRAWINGS

FIG. 3 is an enlargement of the proximal end of FIG. 2.

DETAILED DESCRIPTION OF THE PREFERRED EMBODIMENTS

A typical stent is formed with a wire segment which is formed into a sinusoidal wave form helix pattern the length of the stent by a means such as passing the wire through gears such as those disclosed in U.S. Pat. No. 2,153,936 issued to Owens et al. A typical coronary stent may have the following dimensions. The stent wire can have a diameter of about 0.001 inches to about 0.015 inches. The preferred form of the sinusoidal wave of the wire segment is a length of about 0.150 inches to about 0.090 inches and a wave amplitude of between about 0.050 inches and about 0.080 inches. Any wave length and amplitude combination that would provide adequate vessel hoop strength and vessel coverage is appropriate. The stent 10 must expand evenly and permit the balloon 35 to expand evenly. The stent 10 of this invention and balloon 35 can be transported via a standard #7 or #8 French guiding catheter. Once on location, the stent 10 can be expanded radially by the expansion of the balloon 35; a ratio of 2.75:1 can be achieved with a wire diameter of approximately 0.005 inches and an initial stent diameter of approximately 0.060 inches.

Figure 1:
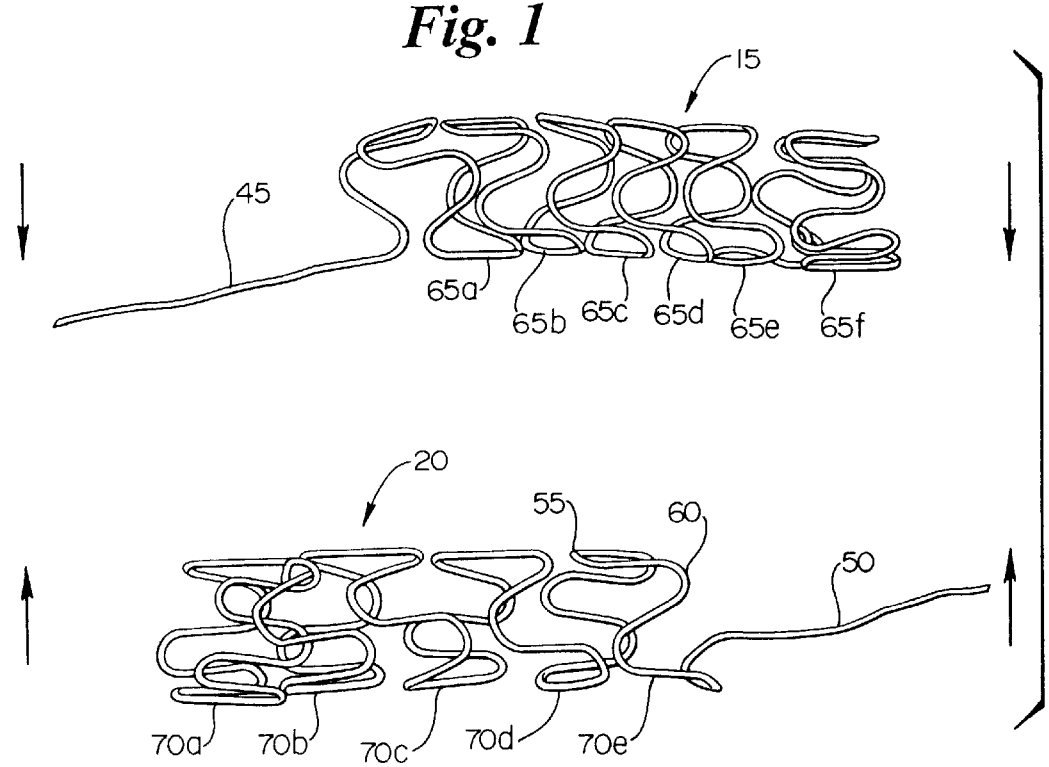
FIG. 1 is a perspective view of a first and second wire segment.
Figure 2:
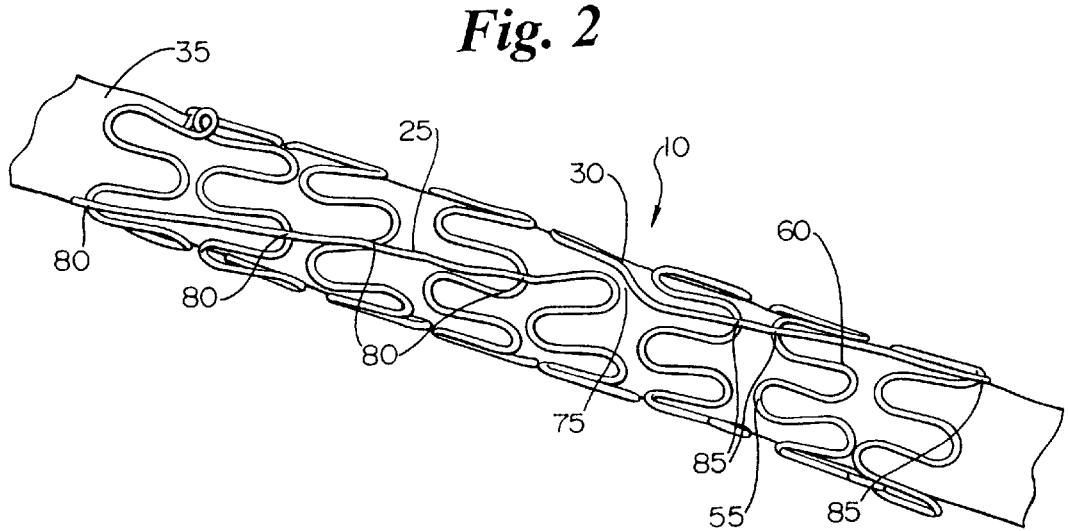
FIG. 2 is a perspective view of an assembled first and second wire segment forming a stent on a balloon according to the invention.

The present invention shown in FIG. 1, depicts a radially expandable first wire segment 15 and a second wire segment 20 in the form of a hollow cylinder defined by a sequence of wire elements 65a–f on first wire segment 15 and elements 70a–e on the second wire segment 20. Each of the first wire elements 65a–f and the second wire elements 70a–e extend 360 degrees around the cylinder. The wire elements have extendible, sinusoidal zig-zags formed by smooth bends such as alternating peaks 60 and valleys 55 as seen in FIGS. 1–3. As shown, the peaks 60 and valleys 55 are shaped in a generally longitudinal direction along the cylinder at one point and then reverse their direction so that the peaks 60 and valleys 55 may open as the wire element 70a is expanded. Also as shown, the wire elements 65a–f and 70a–e are uniformly spaced along the cylinder. Stent 10 is centrally located and positioned with respect to the length of balloon 35. The stent 10 elements are evenly spaced so that when the stent 10 is expanded, the stent 10 will provide even support inside vessel, and resist external loading.

The dual stent is actually two stents each with an end having a straight piece of wire (tails 45, 50) extending from each half stent (first and second wire segments 15 and 20). The two half stents are joined so that the straight tails 45, 50 are on the inside ends of first and second wire segments 15 and 20.

The first wire segment 15 has a straight tail 45 at its proximal end which extends proximally and longitudinally. The second wire segment 20 has a straight tail 50 at its distal end which extends distally and longitudinally. The tail 45 of the first wire segment is slid over the distal end of the second wire segment 20 forming a rib 25 along the exterior of the first wire segment 15. The tail 50 of the second wire segment 20 is slid over the proximal end of the first wire segment 15 forming a rib 30 along the exterior of the second wire segment 15. The ribs 25 and 30 are affixed by any conventional means such as by resistance welding at one or more crossing points 80, 85 including up to each crossing 80, 85 as shown in FIG. 2. The advantage of this design is that having the tail 45 of the first wire segment affixed at crossing 80 to one or more elements 70a–e of the second wire segment 20 as well as the tail 50 of the second wire segment affixed at crossing 85 to one or more elements 65a–f of the first wire segment 15 helps control the strength of the stent 10 as it is expanded on a balloon 35 yet maintains the stent 10 flexibility without resulting in longitudinal compression at the center of the stent when expanded.

The gap 75 between ribs 25 and 30 results in more flexibility at the center of the stent 10 thereby permitting tortuous vessels to be more easily navigated. The ribs 25 and 30 control the length of the stent as is expands on a balloon thus preventing it from shortening or lengthening. This is particularly useful in reducing the dumb bell effect hereinafter described. If the proximal or distal end of the stent 10 snags, ribs 25 and 30 will prevent the stent 10 from unraveling.

As stent metal mass increases there is a tendency towards longitudinal compression at the center of the stent when expanded resulting in a dumb bell effect. The increased metal mass creates more radial hoop strength which in turn increases the amount of force required to expand the stent 10. The center of the stent has more radial hoop strength than the ends of the stent 10. The balloon expands first at the distal and proximal ends before expanding the center which is covered by the stent. This creates a dumb bell shaped balloon. With the stent ends expanding first, the stent slides down the expanded balloon ends toward the center of the balloon which is as yet unexpanded because of the stent's increased radial hoop strength in the center. As the proximal and distal ends of the balloon expand to approximately two-thirds of normal expansion diameter, the mid-section of the balloon begins to expand. When the balloon ends have expanded completely, the stent may have been compressed to approximately one-half of its original crimped length. Because the stent is compressed toward the center of the balloon, complete balloon expansion may not be possible. Ribs 25 and 30 maintain the uniform spacing between the elements of 65a–f and also of 70a–e and reduce the dumb bell effect. This becomes more important as stent length increases.

FIG. 2 depicts ribs 25, 30 aligned on an angle across stent 10 as opposed to the longitudinal axis. The angle is a consequence of finding a straight line along which to weld the ribs 25, 30 which will yield the greatest number of crossings 80. The angle yields the greatest number of crossings 80 because the sinusoidal wave form when helically wound around a mandrel to form the cylinder has a barber poll effect. More crossings 80 are desirable to reduce the dumb bell effect and retain uniform spacing of elements 65a–f and 70a–e.

A forming mandrel sequence can provide a gradual reduction in the stent 10 outer diameter by the use of applied finger pressure under microscopic observation. The outer diameter reduction can be done before or after the tails 25, 30 are welded to the stent 10. It may be advantageous to reduce the outer diameter after the tails 25, 30 are welded depending on what type of welding technique is used. If an electrode is necessary in the stent 10 lumen to accomplish the spot welding, then it may be advantageous to have a larger stent lumen diameter and reduce the diameter after spot welding.

For a coronary sized stent it is possible to go directly from a 0.150 inch stent outer diameter to a 0.065 inch stent outer diameter by placing stent 10 directly onto the balloon 35 from the forming mandrel and make an acceptable stent, but it is more difficult to maintain proper alignment of the stent wires by doing so. Thus it is preferred that the stent 10 is further processed from a 0.150 inch diameter forming mandrel by pressing it onto a 0.100 inch diameter forming mandrel, thereafter pressing it onto a 0.080 inch diameter forming mandrel and finally pressing it onto a 0.065 inch diameter forming mandrel before being applied to the balloon 35. Those skilled in the art would recognize that a variety of acceptable mandrel sizes could be used in the forming sequence depending on the desired stent size.

The stent 10 is removed from the mandrel and placed over a suitable expandable diameter device such as an inflatable balloon 35 which is typically used for angioplasty procedures. Applicant's stent 10 can be used for both coronary and peripheral procedures. A stent can be implanted during a single angioplasty procedure by using a balloon catheter bearing a stent 10 which has been crimped by hand or with a suitable crimping tool (not shown) onto the balloon 35. Manually squeezing the stent 10 over the balloon 35 is also acceptable.

The balloon expandable stent 10 can be made of an inert, biocompatible material with high corrosion resistance that can be plastically deformed at low-moderate stress levels such as tantalum, the preferred embodiment. Other acceptable materials include stainless steel, titanium ASTM F63-83 Grade 1, niobium or high carat gold K 19–22. A self-expanding device can be made by the use of superelastic (nickel titanium) NiTi such as Nitinol manufactured by Raychem or Forukawa.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Stent |
| 15 | First Wire Segment |
| 20 | Second Wire Segment |
| 25 | Rib First Wire Segment |
| 30 | Rib Second Wire Segment |
| 35 | Balloon |
| 45 | Tail First Wire Segment |
| 50 | Tail Second Wire Segment |
| 55 | Valley |
| 60 | Peak |
| 65a-f | Element First Wire Segment |
| 70a-e | Elements second Wire Segment |
| 75 | Rib Gap |
| 80 | First Wire Segment Crossing |
| 85 | Second Wire Segment Crossing |

What is claimed is:

1. A medical device for use in supporting a luminal surface of a human or animal body comprising:

a catheter having a proximal end and a distal end;

a stent mounted on the distal end of the catheter, the stent comprising a hollow cylindrical first wire segment and a hollow cylindrical second wire segment;

the first wire segment forming a plurality of spaced-apart first wire segment elements each extending 360 degrees around a hollow cylinder, each of the first wire segment elements having a plurality of extendible portions which permit the first wire segment elements to be expanded from a first unexpanded diameter to a second, expanded diameter, the first wire segment having a proximal end and a distal end, the first wire segment proximal end having a straight tail extending proximally and longitudinally therefrom;

the second wire segment forming a plurality of spaced-apart second wire segment elements each extending 360 degrees around a hollow cylinder, each of the second wire segment elements having a plurality of extendible portions which permit the second wire segment elements to be expanded from a first unexpanded diameter to a second, expanded diameter, the second wire segment having a proximal end and a distal end, the second wire segment distal end having a straight tail extending distally and longitudinally therefrom;

the proximal end of the first wire segment abutted to the distal end of the second wire segment such that the tail of the first wire segment longitudinally extends along the length of the second wire segment and the tail of the second wire segment longitudinally extends along the length of the first wire segment with one or more elements of the first wire segment being attached to the tail of the second wire segment with each such attachment forming a second wire segment crossing, and one or more elements of the second wire segment being attached to the tail of the first wire segment with each such attachment forming a first wire segment crossing; and a means on the catheter for releasing the stent from the catheter in the expanded diameter.

2. The medical device according to claim 1 wherein the extendible portions include smooth bends.

3. The medical device according to claim 2 wherein the smooth bends are sinusoidal.

4. The medical device according to claim 1 wherein the first and second wire segments are formed of a biocompatible metal that can be plastically deformed at low to moderate stress levels.

5. The medical device according to claim 1 wherein the first and second wire segments are formed of a super-elastic metallic material.

6. The medical device according to claim 1 wherein the means for releasing the stent in expanded form comprises a balloon.

7. The medical device according to claim 1 wherein a means for attaching the elements of the first and second wire segment to the tail of the first and second wire segment includes welding.

8. The medical device according to claim 1 wherein each element of the first wire segment is attached to the tail of the second wire segment and each element of the second wire segment is attached to the tail of the first wire segment.

9. The medical device according to claim 8 wherein the tail of the second wire segment is positioned over the elements of the first wire segment and the tail of the first wire segment is positioned over the elements of the second wire segment such that the number of first and second wire segment crossings is maximized.

10. The medical device according to claim 1 wherein the tail of the first wire segment and the tail of the second wire segment form a straight line.

11. The medical device according to claim 10 wherein the tail of the first wire segment and the tail of the second wire segment form an angle to the longitudinal axis of the stent.

* * * * *